(12) United States Patent
Smith et al.

(10) Patent No.: US 6,187,213 B1
(45) Date of Patent: Feb. 13, 2001

(54) MARKING DIAMOND

(75) Inventors: James Gordon Charters Smith, High Wycombe; Martin Cooper, Marlow, both of (GB)

(73) Assignee: Gersan Establishment, Liechtenstein (DE)

(*) Notice: Under 35 U.S.C. 154(b), the term of this patent shall be extended for 0 days.

(21) Appl. No.: 09/000,110

(22) PCT Filed: Jul. 17, 1996

(86) PCT No.: PCT/GB96/01712

§ 371 Date: May 15, 1998

§ 102(e) Date: May 15, 1998

(87) PCT Pub. No.: WO97/03843

PCT Pub. Date: Feb. 6, 1997

(30) Foreign Application Priority Data

Jul. 17, 1995 (GB) ................................................ 9514558

(51) Int. Cl.⁷ ............................. B44C 1/22; B23K 26/00
(52) U.S. Cl. ................................. 216/28; 216/65; 216/81
(58) Field of Search ........................... 216/28, 65, 66, 216/81

(56) References Cited

U.S. PATENT DOCUMENTS

| 3,527,198 | 9/1970 | Takaoka | 125/30 |
| 4,032,861 | 6/1977 | Rothrock | 331/94.5 |
| 4,056,952 | * 11/1977 | Okuda | 63/32 |

(List continued on next page.)

FOREIGN PATENT DOCUMENTS

| 0 054 840 | 6/1982 | (EP) . |
| 0 264 255 | 4/1988 | (EP) . |
| 0 419 087 A1 | 3/1991 | (EP) . |
| 0 552 321 | 6/1992 | (EP) . |
| 0 567 129 A2 | 10/1993 | (EP) . |
| 0 749 799 A2 | 12/1996 | (EP) . |
| 612868 B1 | * 7/1998 | (EP) . |
| 2 248 575 | 4/1992 | (GB) . |
| 2 275 788 | 9/1994 | (GB) . |
| 58-086 924 | 5/1983 | (JP) . |
| 6-247793 | * 9/1994 | (JP) . |
| 90/03661 | 4/1990 | (WO) . |
| 92 09876 | 6/1992 | (WO) . |

OTHER PUBLICATIONS

Author unknown. "New Distributors For Lazare Diamonds", Diamond International, p. 25 Jan./Feb. 1992.

Znotins, Norris, "Industrial Excimer Lasers; issues and answers", Proceedings of SPIE, 1988, vol. 894, pp. 9–15.

Ageev, "Laser Processing of a Diamond and Diamond–Like Films", Materials & Manuf. Processes, 8(1), 1–8 (1993), pp. 1–8.

Armeyev, "Direct Laser Writing of Microstructures in Diamond–Like Carbon Films", Materials & Manuf. Processes, 9(1), 9–17 (1993) pp. 7–17.

Bar–Isaac Thesis, pp. 92–97 Sep. 1975.

Bruton, "Diamonds", 1981, p. 409.

Crater, "Multiple Roles For Laser Marking", Laser & Optronics, Oct. 1987, vol. 6 No. 10, pp. 63–65.

(List continued on next page.)

Primary Examiner—Randy Gulakowski
Assistant Examiner—Anita Alanko
(74) Attorney, Agent, or Firm—Cesari and McKenna, LLP

(57) ABSTRACT

In order to produce on the table of a diamond gemstone (7), an information mark which is invisible to the naked eye using a ×10 loupe, an ultraviolet laser (1) having a wavelength of 193 nm is used in association with a mask (2) to irradiate the surface of the stone (7) at a fluence of less than 2 J/cm² per pulse and with not fewer than 100 pulses, in the presence of air which reacts with the diamond (7) and causes the mark to be formed without any darkening which is visible when viewing using a microscope.

21 Claims, 3 Drawing Sheets

U.S. PATENT DOCUMENTS

| | | | |
|---|---|---|---|
| 4,200,506 | * | 4/1980 | Dreschhoff et al. ............... 204/157.1 |
| 4,260,649 | | 4/1981 | Dension et al. ..................... 427/53.1 |
| 4,392,476 | | 7/1983 | Gresser et al. .......................... 125/30 |
| 4,425,769 | * | 1/1984 | Hakoune .................................. 63/32 |
| 4,467,172 | | 8/1984 | Ehrenwald et al. ................. 219/121 |
| 4,478,677 | | 10/1984 | Chen et al. ........................... 156/635 |
| 4,511,783 | | 4/1985 | Burgemeister ....................... 219/121 |
| 4,684,781 | | 8/1987 | Frish et al. ........................... 219/121 |
| 4,842,782 | | 6/1989 | Portney et al. ....................... 264/1.4 |
| 4,912,298 | | 3/1990 | Daniels et al. .................. 219/121.69 |
| 5,002,899 | | 3/1991 | Geis et al. ............................ 437/173 |
| 5,012,067 | | 4/1991 | Sato et al. ........................ 219/121.72 |
| 5,149,938 | | 9/1992 | Winston et al. ................ 219/121.69 |
| 5,160,405 | | 11/1992 | Miyauchi et al. ................... 156/643 |
| 5,334,280 | | 8/1994 | Anthony et al. ....................... 156/635 |
| 5,344,526 | | 9/1994 | Nishibayashi et al. .............. 156/643 |
| 5,410,125 | * | 4/1995 | Winston et al. ................ 219/121.69 |
| 5,419,798 | | 5/1995 | Anthony et al. ...................... 156/345 |
| 5,458,733 | | 10/1995 | Tessmer et al. ....................... 216/67 |
| 5,483,038 | | 1/1996 | Ota et al. ......................... 219/121.69 |
| 5,760,367 | * | 6/1998 | Rosenwasser et al. ......... 216/121.69 |

OTHER PUBLICATIONS

Dance Article "Novel Excimer Laser System Marks Wires On–The–Fly", Laser Ffocus Word, May 1990.

Deckman, "Micromachining Applications for ICF Target Fabrication", J. Vac. Sci. Technol., 18(3), Apr. 1981 pp. 1171–1174.

Geis, Rothschild et al., "Electrical, Crystallographic, and Optical peoperties of ArF Laser Modified Diamond Surfaces", Appl. Phys, Lett, 355(22), Nov. 27, 1989, pp 2295–2297.

Harano, Ota, Fujimori "Diamond Processing By Excimer Laser Ablation", Conference Proceedings of Advances in New Diamond Science and Technology, MFU, Tokyo 1994, pp 497–500.

Kahlert, Sowada, Basting "Excimer Lasers for Material processing; Results and Industrial Application", Proceedings of the SPIE, 1988 vol. 1023, pp. 171–178.

Klimt, "Review of Laser Marking and Engraving", Lasers and Optronics, Sep. 1988, vol. 7, No. 9, pp 61–67.

Kononenko, "KrF of Excimer Laser Etching of Diamond–Like Carbon Films", Proceedings of SPIE—Inter. Soc. of Optical Eng. vol. 1759, 1992.

Konov, "Pulse–Periodic Laser Etching of Diamond–Like Carbon Coatings" Jou. J. Quantum Electron 21(16) Oct. 1991 pp. 1112–1115.

Konov, "Light–Induced Polishing of an Evaporating Surface" Sov. J. Quantum Electron 21(4) Apr. 1991, pp 442–444.

Marsh, "Beaming in on a Sales Explosion", Financial Times, Sep. 2, 1986, p. 13.

Nilson, "Laser Marking Via Mask Projection", Proc Materials Processing Symposium ICALEO '82, Boston, MA Sep. 20–23, 1982, 1982 Laser Institute of America, vol. 31, pp 17–24.

Dr. R L Penny's Technique—not published.

Pruess and Stuke, "Subpicosecond Ultraviolet Laser Ablation of Diamond, Nonlinear Properties at 248 nm and Time–Resolved Characterisation of Ablation Dynamics", Appl. Phys. Lett. 67(3), Jul. 17, 1995, pp. 338–340.

Rothschild, Arnone, Ehrlich, "Excimer–Laser Etching of Diamond and Hard Carbon Films by Direct Writing and Optical Projection", Journal of Vacuum Science and Technology, Jan./Feb. 1986, vol. 84, No. 1, pp. 310–314.

Rothchild, Arnone, Ehrlich, "Excimer Laser Projection Patterning with and without Resists; Submicrometer Etching of Diamond and Diamond–Like Carbon Resis", SPIE vol. 633, Optical Microlithography V (1986), pp. 51–57.

Sercel, Sowada, "Why Excimer Lasers Excel in Marking", Lasers and Optronics, Sep. 1988, vol. 7, No. 9, pp 69–72.

Sercel, Sowada, Kahlert, Basting, Austin, "Industrial Microprocessing Applications of Excimer Lasers", Proceedings of SPIE, 1988 vol. 998, pp 76–83.

Sowada, Kahlert, Basting, Lambda Industrial Report No. 4, Oct. 1988, pp. 1–6.

Sowada, Kahlert, Gerhardt, basting, Laser and Optoelektronik: 29(2), 1988, pp 96–101.

Tezuka, "Processing of CVD Diamond Films by YAG Laser", J. of JAP Soc. of Precision Eng. vol. 56, No. 12 Dec. 1990.

Willis, "Techniques and Applications of Laser Marking", Proc. 1st Int. Conf. Lasers in Manufacturing, Brighton, Nov. 1–3, 1983, IFS/North Hiland, pp 53–62, 1983.

Wright, "Lasers for Materials Processing: Past, Present and Future", Welding and Metal Fabrication, Aug.–Sep. 1987, vol. 55 No. 6, pp 275–288.

Znotins, "Industrial Applications of Excimer Lasers", Proceedings of SPIE 1986, vo.. 668, pp 339–346.

Znotins, Poulin, Reid, Excimer Lasers: an emerging technology in materials processing:, Laser Focus, May 1987, vol. 23, pp 54–70.

"Guide for Material Processing By Lasers", Laser Institute of America, Second Edition, 1978, pp 8–27 to 8–35.

Spectrum Technologies Data Sheet, Sep. 1990, entitled "Cable Printing and Identification Systems CAPRIS 500; Excimer Laser Cable Marker".

Marketers Place Diamonds Among Other Brand Name Products, New York Diamonds, Spring 1990, 38–44.

* cited by examiner

MARKING DIAMOND

BACKGROUND TO THE INVENTION

The present invention relates to a method of producing on a polished facet of a diamond gemstone an information mark which is invisible to the naked eye, comprising using ultraviolet radiation or other radiation to irradiate the surface of the respective portion of the stone. "Invisible to the (naked) eye" means invisible to the (naked) eye of the expert or trained diamond grader. The information mark (which may be called an indicium) may be an identification mark for the diamond but need not identify a particular diamond and in general could give other information such as a quality or trade mark. Normally, the information mark will be a complex mark, not say a simple dot.

Such information marks are discussed in U.S. Pat. No. 5,410,125, from column 1, line 40 to column 2, line 2, but the technology of producing information marks on diamonds is also discussed in U.S. Pat. No. 4,392,476, U.S. Pat. No. 4,467,172, U.S. Pat. No. 5,149,938 and U.S. Pat. No. 5,334,280, and like technology is discussed in U.S. Pat. No. 4,912,298 in relation to spectacle lenses. In EP 0 567 129 A, U.S. Pat. No. 4,478,677, WO 90/03661, a paper by Geis et al in Appl. Phys. Lett. 55(22), pages 2295 to 2297, a paper by Harano et al in Advances in New Diamond Science and Technology, MYU Tokyo 1994, pages 497 to 500, a paper by Rothschild et al in J. Vac. Sci. Technol. B4(1), January/February 1986, pages 310 to 314, a paper by Rothschild et al in Proceedings of the SPIE, 1986, vol 633, Optical Microlithography V (1986), pages 51 to 57, a paper by Sercel et al. in Lasers & Optronics, September 1988, pages 69 to 72, and a paper by Sercel et al in Proceedings of the SPIE, vol 998, pages 76 to 83, there are discussions of similar technology.

There are relatively few published papers on the interaction of good quality gem diamond with intense pulsed ultraviolet lights such as those generated by excimer lasers. If diamond is discussed, most papers are concerned with polycrystalline diamond or "diamond like" films grown by chemical vapour deposition (CVD). The CVD material is often of poor optical quality and may contain significant amounts of carbon bonded in a graphite like ($sp^2$) configuration rather than the pure diamond ($sp^3$) configuration. Owing to the difference in the structures, these CVD materials are not likely to interact with ultraviolet radiation in the same way as good quality gem diamond material.

It is desirable to be able to produce the information mark in a manner which is not complex, which gives consistent results, which does not take too much time, which causes little pollution, and which gives no risk of damage to the diamond; it is also desirable to produce an even less visible mark which however with suitable magnification and viewing conditions is distinct and readable or identifiable.

The Invention

According to the method of the invention, an information mark which is invisible to the naked eye is produced on a polished facet of a diamond gemstone by irradiating the respective portion of the facet surface with radiation having a wavelength less than about 400 nm, in the presence of a reagent which reacts with the irradiated portion of the facet surface and causes a mark to be formed, the fluence of the radiation being below the level at which substantial darkening is present in the formed mark or below the level at which the formed mark detracts from the clarity grade of the diamond or being below the ablation threshold of the diamond. The invention also provides gemstones having a polished facet marked by the method, and apparatus for carrying out the method, comprising: means for mounting a diamond gemstone; a radiation source and optical means arranged to irradiate the surface of a polished facet of the gemstone with pulsed irradiation having a wavelength less than about 400 nm with a fluence at the location irradiated of not more than about 3 $J/cm^2$ per pulse and with not fewer than about 100 pulses per location irradiated; and means for having present at the location irradiated a reagent which reacts with the irradiated portion of the facet surface and causes a mark to be formed without there being substantial darkening in the formed mark. In the method of the invention, the conditions suitable for etching are produced by irradiating the desired region or regions of the sample with intense, preferably ultraviolet light, such as the pulsed irradiation produced by ArF excimer lasers. As the irradiation can be selectively applied only to the regions where etching is desired, no etch resist need be applied to the surface.

Ablation

Ablation as used herein is a process in which intense radiation, such as that produced by a pulsed ultraviolet laser, is absorbed in a thin layer at the surface of the diamond, either causing the layer to be transiently heated to a high temperature, or breaking the chemical bonds within that layer, so that a portion of the layer is vaporised or ejected from the material. It essentially involves a physical transformation of the material from a solid to a vapour without the involvement of any other reagents. Once vaporised, the material may react chemically with any reagents present. The hot carbon vaporised during ablation will readily react with an oxygen ambient to produce carbon monoxide and carbon dioxide. However the ablation would still take place in the absence of such a reagent. It is generally thought that ablation will not take place if the fluence of the pulsed irradiation (the energy per pulse per unit area of the irradiated surface) is below a threshold value.

Ablation at anomalously low threshold fluences can be obtained with CVD diamond and diamond-like films. The presence of non-diamond carbon in these materials can be expected to have a detrimental effect on the resistance of the material to the irradiation.

Phase Transformations

Diamond tends to transform to non-diamond forms of carbon when heated to high temperatures. This can lead to a build-up of a partially non-diamond layer in the irradiated region. Once the layer has started to form, it tends to absorb the irradiation more strongly than would be expected of clean diamond. Further energy pulses may then be capable of ablating the modified layer. The apparent ablation threshold for such a modified surface would be lower than for the original diamond. Once ablation is established, the process of forming non-diamond carbon phases continues at the bottom of the mark, so that ablation is sustained.

Darkening

As used herein, "darkening" is the increased optical density caused by the formation of grey or black marks or deposits due to the presence of amorphous carbon or other non-diamond carbon, for instance caused by deposition of vapourised carbon or by phase transformation to form a layer of modified material at or below the diamond surface. Substantial darkening is darkening that is severe enough to make the mark sufficiently visible enough to detract from the value of the stone, normally considered to be darkening that renders the mark visible to an expert using a ×10 loupe (ie to the expert naked eye aided with a ×10 loupe) or (a more stringent test) visible under a ×10 microscope such as a GIA "Gemolite" (trade mark).

Diamonds are graded according to their degree of clarity. Various grading scales are recognised, such as that used by the GIA, but all the scales are in reasonable agreement with each other. A flawless diamond (GIA FL) does not have any inclusions, cracks, or other defects inside the diamond and no defects on the surface of the diamond that would inhibit the free passage of light through the diamond. The test is based on features observable with a ×10 loupe, which is the loupe used by jewellers generally features with a maximum dimension of less than 5 microns are not detectable with a ×10 loupe. If a mark is produced on say the table of such a diamond that is observable with a ×10 loupe, the clarity grade of the diamond, and hence its value, would be reduced and this would not be desirable. Any darkening will tend to make the marks much more apparent. Thus in addition or in the alternative undesirable darkening may be considered to be darkening that detracts from the clarity grade of the diamond. For diamonds of poorer clarity, one could tolerate a far more visible mark since the presence of the mark that is for example just visible with a ×10 loupe would have less effect on a diamond that already had clearly visible inclusions in it.

Even less darkening can be achieved using the invention. For instance, no darkening may be visible using a ×10 or ×100 or ×200 optical microscope such as a gemmological microscope or using a ×50 or ×200 or ×800 metallurgical microscope such as the Zeiss Ultraphot manufactured by Carl Zeiss; there may be no detectable non-diamond or no non-diamond at all.

The modified material formed by phase transformation tends to absorb light. In absolute terms, a layer of modified material may be said to exhibit substantial darkening if say 5% or 10% of light is absorbed by the layer, though this has not been quantitatively determined and is not limiting. The modified material does not have an undisrupted diamond structure, though it may be crystalline, and thus some non-diamond carbon is present. The appearance of the modified material however depends on the morphology of the layer. If it is essentially flat, it can have almost a metallic lustre, similar to that possessed by crystalline graphite. It is possible that a greyish modified layer is initially produced and is immediately etched away by reaction with the gas to provide a clean mark if the rate of removal is potentially much faster than the rate of production of the modified layer. Nonetheless, at the end of etching, a very thin modified layer may remain at the bottom of the mark, which would not be termed substantial darkening; in other words, a very thin flat modified layer as part of an information mark on a facet of a polished diamond gem may not be visible enough to be detrimental to the value of a stone, although it would be undesirable.

Although the invention is primarily concerned with producing marks which are invisible to the naked eye and also invisible to the naked eye aided with a ×10 loupe, it is possible that in the future such marks, being in the nature of hall marks, may become acceptable even though they are visible with a ×10 loupe or to the naked eye alone. Nonetheless, the specific procedures of the invention are advantageous in enabling such more visible marks to be produced without darkening or excessive darkening and thus without making the marks obtrusive.

Advantages of the Invention

By avoiding substantial or undesirable darkening, the visibility of the marks can be greatly reduced. As there is no undesirable darkening, there is no necessity afterwards to remove any black or grey marks (for instance by chemical processes such as acidization), which may in any case be impossible if the darkening is due to phase transformation within the diamond. As there is no requirement to remove black or grey marks, set stones can be marked. The possibility of marking set stones is also provided by the relatively low energy which can be used, avoiding excessive heating of the stone as a whole (it is believed that the rise in temperature of the stone as a whole is of the order of 0.5° C. say for a 20 pt. stone (0.04 gm), though this varies according to the size of the stone and the size of the mark applied); the relatively low energy which can be used also avoids any necessity for cooling, and avoids risking damage to the stone. Thus the invention enables diamonds to be marked without forming any undesirable by-products or damaging the diamond in any other way.

The invention also enables very shallow marks to be produced in a controllable manner. The lack of substantial darkening and the shallowness enables the marks to be invisible to the eye, and they are preferably invisible to the naked eye aided with a ×10 loupe. However, the marks can be easily visible using a microscopy technique that highlights the edges of the mark, such as dark field illumination. A metallurgical microscope can be used for such techniques. Alternatively, one can obtain an accurate three-dimensional image of the mark using an interference microscope such as the "Micromap" (trade mark) produced by Micromap of Tucson, Ariz. As there is no substantial darkening, the visibility of the mark is achieved purely by the depth of the mark. As the mark is invisible to the naked eye, it can be on the table of a good quality polished diamond (preferably in the middle or specifically in the geometric centre, where it is easy to find) without any detraction from the value of the diamond, i.e in a position which is accessible for marking and for checking when the diamond is mounted in a setting. Nonetheless, if desired, the mark could be provided on another facet, for instance on a girdle facet.

Information Mark Shape and Size

The invention enables very complex marks to be applied with fine resolution, for instance marks having areas of different depths or fine line patterns or different cross-sectional profiles, so that the marks can contain much information and cannot easily be copied. The shape of the information mark can be formed by any suitable irradiation technique. However, as laser scanning may be too slow in practice, a masking technique can be used, and such techniques are well known. There are a number of known ways of eroding or burning to different depths, such as a) the use of a sequence of mutually aligned masks to expose different parts of the sample to different doses of irradiation, or b) the use of half-tone masks (normally dots on the mask which are not resolved by the optical system), or c) the use of masks of varying transmission. Though the cross-sectional profile of the mark is preferably rectangular, and much wider than deep, this can be varied as appropriate and the profile could be other than rectangular. A preferred mark has a character height of about 50 microns, a character line width of 2–3 microns and a total width of 200–250 microns, but this can be varied as appropriate. The marks preferably have a depth of not more than about 100 or 50 or 30 nm, and preferably have a depth of not less than 1, 3, 5 or 8 nm, the preferred depth being between about 10 and about 20 nm. Deeper marks, eg up to 1 micron or more, may be produced but may be more readily visible and slow to process.

Etching

Although the reaction mechanism is not known, the diamond is etched, diamond being removed by the radiation-induced chemical reaction between the stone and the gas, i.e. the radiation produces conditions at the surface of the stone which enable the reagent to react with the stone, possible with the formation of the modified layer referred to above. Under certain conditions, eg an insufficient oxygen partial pressure when working on certain crystallographic faces of the diamond, a slightly grey or greyish layer may be observed at the surface of the diamond, believed due to the modified layer referred to above not being largely etched away; a greyish layer of this thickness is often considered undesirable and may be removed or avoided by increasing the partial pressure of oxygen. In the case of oxygen, it is thought that oxygen becomes adsorbed onto the diamond surface which then further reacts with the surface when it is heated by the irradiation, to liberate carbon monoxide or carbon dioxide. However it may be that the presence of the ultraviolet light of the irradiation plays a significant role in the reaction itself as such light is capable of breaking the various chemical bonds involved in the process, or that oxygen free radicals created by the irradiation are significant in the process.

In general, as the invention is worked below the ablation threshold, it is believed that the reagent reacts directly with the diamond, and does not remove amorphous soot-like deposits, and that amorphous carbon is not formed. It is believed that the respective portion of the surface of the stone is heated to a temperature less than the graphitisation temperature, which for most diamonds is about 1800° C., though in the presence of air, a black layer may start to form at about 700° C.

Reagents

Any suitable reagent can be used for reacting with the diamond, and there is a discussion of possible gases in U.S. Pat. No. 5,334,280. A preferred reagent is a fluid, preferably a gas, and the preferred gas is an oxidising gas such as air; though it is possible to use gases other than oxygen, the etching process is less effective if oxygen is excluded from the irradition zone.

Radiation

Any suitable radiation source can be used, but lasers are the only suitable sources at present commercially available. Any suitable wavelength can be used, but the wavelength is preferably ultraviolet, ie shorter than about 400 nm. As all known diamonds are opaque to irradiation below about 225 nm (and most are opaque to irradiation below about 300 nm), the wavelength, or at least the wavelength of a significant percentage, say more than about 50%, of the energy in the irradiation or in the ultraviolet or visible irradiation, is preferably not greater than about 225 nm or about 300 nm. This results in the irradiation being absorbed only in the surface layer of the stone, penetrating only a few microns into the stone, so that most of the energy is provided for heating the specific portions which are to be marked, avoiding heating up the bulk of the stone to any significant extent. If desired, more than one radiation source can be used.

Pulsing and Etch Rate

It is highly desirable that the radiation source should be pulsed, and the use of multiple pulses makes the process controllable in that the marking depth will be roughly proportional to the number of pulses; if desired, the depth could be monitored during the process using for example a sensitive interferometric technique, with suitable feed-back. If the etch rate varies significantly according to the crystal orientation or diamond type, the orientation and/or diamond type should be determined before initiating etching. It is preferred that there should be a large number of pulses per location or spot irradiated, for instance not less than about 100, 500 or 800 pulses; however, to keep the time within reasonable bounds, it is preferred that there are not more than about 5000 or 3000 or 1500 pulses: a preferred value is about 1000 pulses. Thus a combination of low fluence per pulse and a high number of pulses can be used in order to avoid damage to the stone while providing a mark which is deep enough to be visible using say a microscopy technique. With a high number of pulses, it is possible to work below the ablation threshold and obtain a mark which is visible using a microscopy technique. The removal rate is relatively slow, and is preferably not more than about 0.1 or 0.05 or 0.03 or 0.02 nm per pulse. It is reasonable to expect the maximum etch rate, in the case of pulsed irradiation, to be not more than about one atomic layer per pulse. This would be approximately 0.18 nm per pulse. The maximum etch rate achieved so far is approximately 23% of this value, ie 0.042 nm per pulse. It is possible that this rate may be improved by for example using a different reagent gas or mixture of gases or altering the pressure or concentration of the reagents or using non-gaseous reagents. Further improvements to the rate might be made by maintaining the bulk of the diamond at a temperature either higher or lower than room temperature. As other sources of intense irradiation become available, with different pulse lengths, it may be found that one of these sources are in some way superior to the Argon Fluoride Excimer laser that is currently preferred. The amount removed is preferably not less than about 0.0025 or 0.005 or 0.008 or 0.01 nm per pulse.

The rate of the process is much too slow to be useful for processes such as sawing and the formation of structures deeper than eg 10 microns in diamond. It is however ideally suited for producing very shallow marks on the surface of polished diamonds.

Repetition Rate

The repetition rate is preferably not more than about 500 or 200 Hz, to ensure enough heat dispersion, though in experimental work a repetition rate of about 20 Hz was used.

Fluence

Unless otherwise specified, the fluences are all as at the location irradiated (the energy impinging on the surface of the respective portion of the stone). In order to avoid damaging the stone, ablation is avoided. The fluence should be low, and is preferably not more than about 5 or 3 or 2.5 or 2 or 1.2 $J/cm^2$ (Joules/$cm^2$) per pulse. In the experimental apparatus used, ablation occurred if the fluence exceeded 2–3 $J/cm^2$ per pulse, the exact value depending on the sample, though other apparatus may give somewhat different values. As the etch rate increases rapidly with increasing fluence, it is desirable to use as high a fluence as is compatible with the above requirement to avoid ablation, ie provided the reaction is below the ablation threshold. The fluence is preferably not less than about 0.05 or 0.1 or 0.15 or 0.2 $J/cm^2$ per pulse; the preferred value is about 0.85 $J/cm^2$ per pulse when the pulse length is approximately 30 nanoseconds and the wavelength is 193 nm—this is equivalent to a peak power of $28 \times 10^6$ J/sec/cm$^2$ at the location irradiated. If a different pulse length or wavelength is used, the fluence should be adjusted accordingly. As the fluence is measured per pulse, it is possible that with different technology and much shorter pulse lengths, the desired fluences may be significantly lower than those indicated above.

Diamond Mounting Means

In association with, or independently of, the foregoing, mounting means for mounting a gemstone for treatment of a facet thereof can comprise means (eg one or more planar reference surfaces) defining a reference plane and adjustable gemstone support means for supporting the gemstone with a facet coplanar with the reference plane.

In a simple embodiment, the mounting means can be a support member with a planar surface defining the reference plane, a recess in the planar surface for receiving the gemstone, and a space in said recess for receiving a deformable material between the rear side of the gemstone and the support member.

Preferred Embodiments

The invention will be further described by way of example, with reference to the accompanying drawings, in which.

FIG. 1

Figure 1:
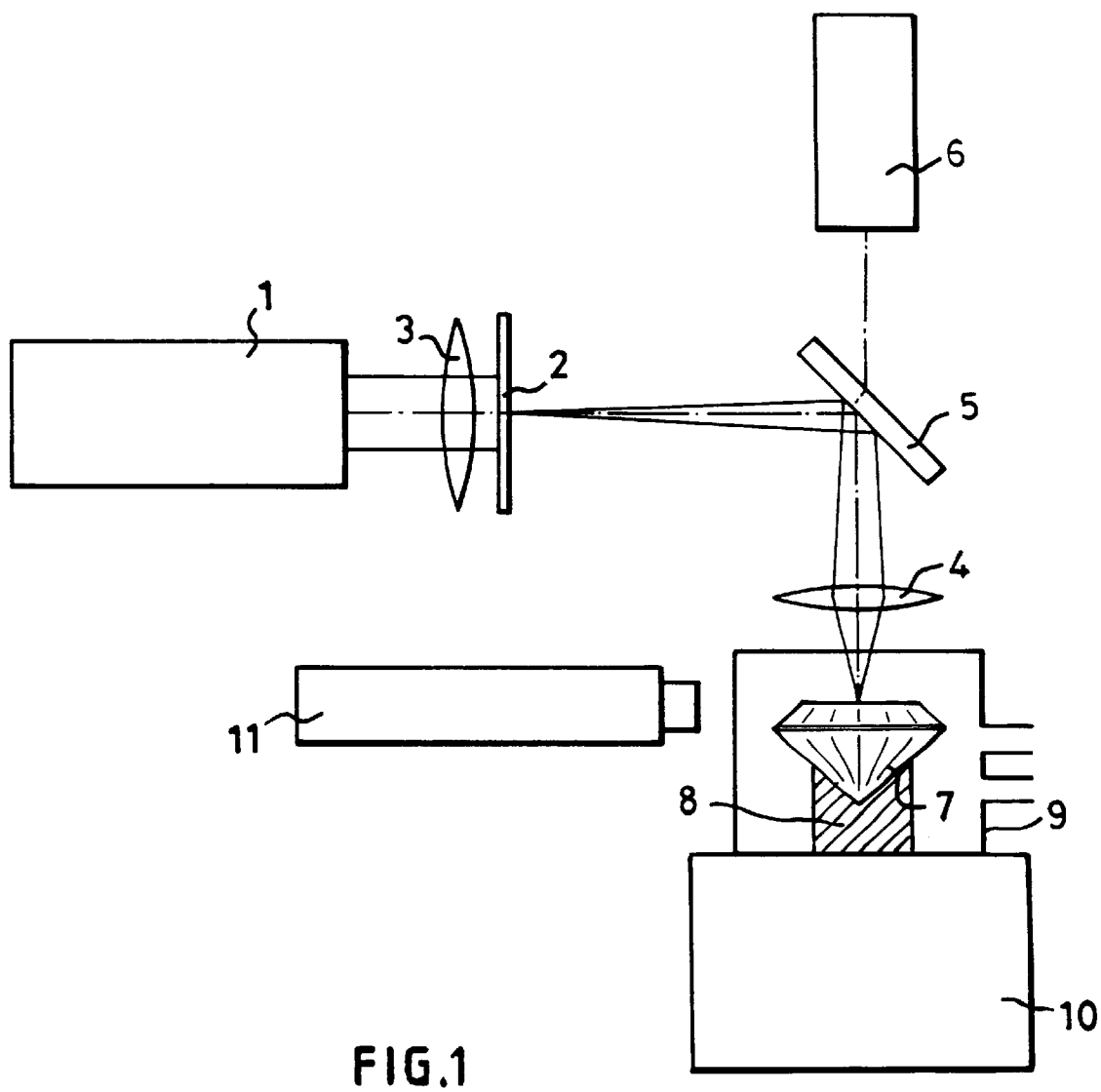
FIG. 1 is a schematic view, partly in section, of first apparatus with which a method of the invention is performed.

An Argon Fluoride excimer laser (wavelength=193 nm) 1, eg a "Questec 2000", was used to illuminate a mask 2 that consisted of a layer of chromium deposited on a fused silica substrate. The transparent regions of the mask 2 consisted of alpha-characters approximately 1.25 mm high. Other types of mask could be used instead and features other than alpha-characters could be on the mask 2.

A field lens 3 was placed behind the mask 2 to direct the laser light into a reducing (objective) lens system 4 in the form of an air-spaced doublet lens of 20 mm focal length, placed 500 mm from the mask 2. Other optical components such as a beam homogeniser and/or a laser attenuator may be placed between the laser 1 and the mask 2 as is known to those skilled in the art of excimer laser lithography.

An ultraviolet reflecting mirror 5 introduces a bend in the optical system in order to allow a camera system 6 such as a CCD camera to view the process and to act as an alignment aid. The ultra-violet mirror 5 is essentially transparent to visible light so a diamond 7 may be viewed through the mirror 5. Other configurations to achieve a similar result may be used as is known by those skilled in the art. Alternatively the mirror 5 and camera system 6 may be omitted.

The reducing lens system 4 forms an image of the mask on the surface of the diamond 7, with a demagnification of x25. Other optical systems, including those incorporating reflecting elements, may be used instead. Other demagnifications may be used, providing that the laser power is adjusted to maintain the fluence at the desired value.

The lens system 4 may be fitted with an aperture stop to control the resolution and depth of focus of the imaging system. The spatial coherence of the imaging system may be modified by controlling how much of the stop is illuminated by the laser beam, as is known to those skilled in the art. This may be achieved for example by altering the configuration of the field lens 3. A highly coherent source may produce artifacts in the image, especially near the edges of features where a "ringing" may be observed. This could be exploited as a security feature. Alternatively, the artifacts may be eliminated by illuminating more of the aperture of the reducing lens. One suitable method of doing this is to incorporate a beam homogeniser between the laser 1 and the mask 3. A higher average fluence may then be employed. This will increase the etch rate without any risk of producing darkening near the edges of the features, where ringing would otherwise occur. The use of a beam homogeniser has the further advantage of ensuring that the mask is uniformly illuminated. The polarisation of the laser may also be controlled to alter the exact nature of the image.

The diamond 7 is a brilliant-cut gemstone, formed by the conventional procedure of sawing a rough stone, bruting, blocking and polishing. The diamond 7 has a table in the conventional manner. The diamond 7 is mounted on a plinth 8 inside a gas cell or enclosure 9 to allow control of the gas atmosphere. The enclosure 9 may be omitted if the marking is conducted in air, or if gas is blown onto the sample from a pipe or nozzle.

The enclosure 9, or the plinth 8 if there is no enclosure 9, is attached to a three axis translation stage 10. The two adjustments perpendicular to the optical axis may be used to position the stone. The third adjustment is used to place the diamond 7 at the focus of the image formed by the reducing lens system 4. This is facilitated by using a microscope 11 to view the position of the table.

Other arrangements may be used such as positioning a plurality of pre-aligned stones on a cassette and marking each in turn. The orientation of the diamond 7 could be different; for instance, its axis could be horizontal. The process may be automated.

FIG. 2

Figure 2:
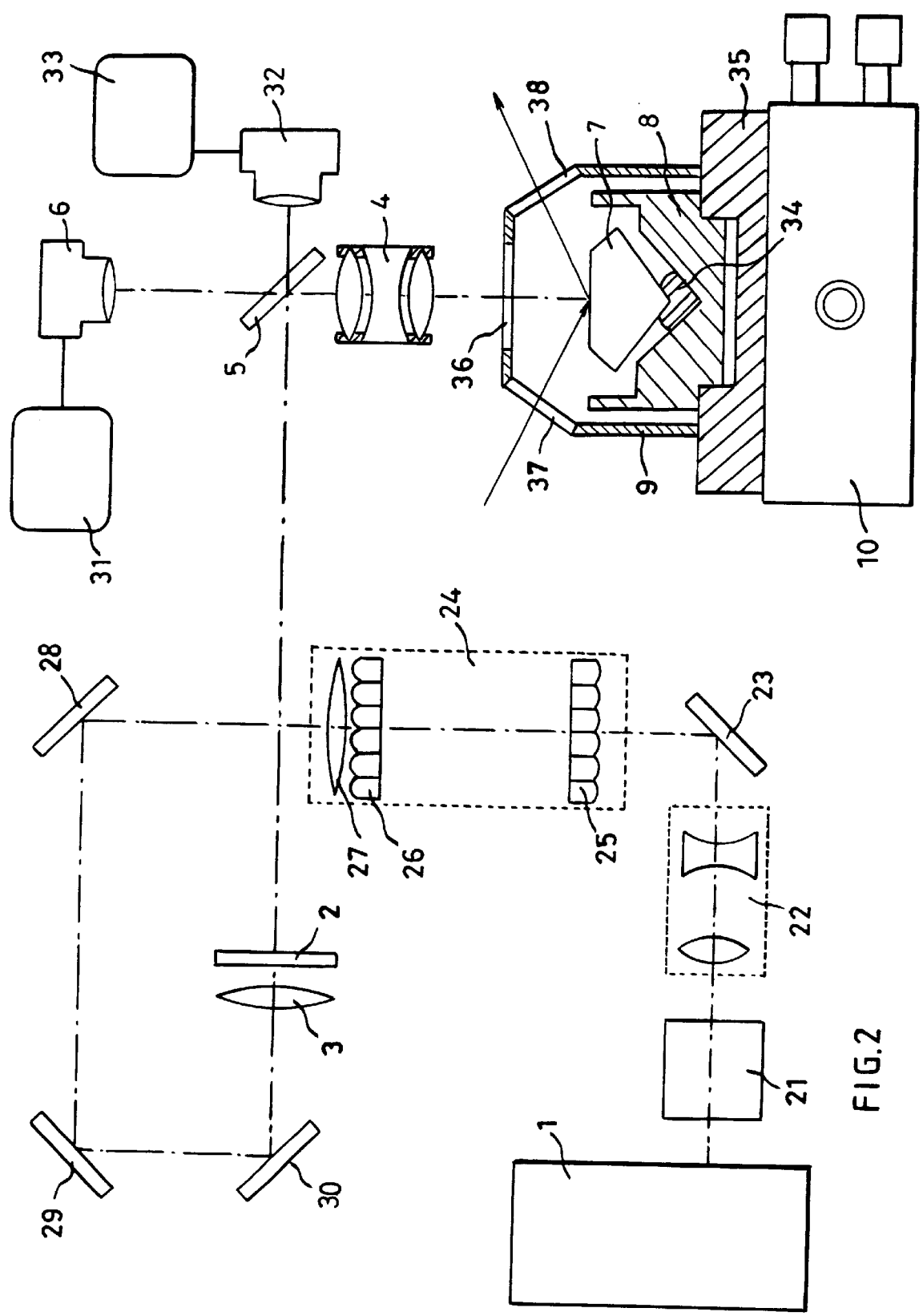
FIG. 2 is a schematic view, partly in section, of second apparatus with which a method of the invention is performed.

In essence, the apparatus of FIG. 2 is similar to that of FIG. 1 and the same references are used for similar items.

A "Compex 205" excimer laser 1 manufactured by Lambda Physik GmbH of Goettingen in Germany was configured to operate with ArF in order to produce pulsed irradiation with a wavelength of 193 nm. The beam produced by the laser was approximately 10 mm wide and 25 mm high. No attempt was made to reduce either the spectral line width or the divergence of the laser, although this could be done if it was considered desirable.

An apparatus supplied by Exitech Ltd. of Long Hanborough in Oxfordshire was used to direct the radiation from the laser onto the diamond to be marked. The beam first enters an adjustable laser attenuator 21. This transmits only a fraction of the incident beam, ultimately allowing the fluence at the diamond surface to be controlled. The remaining radiation then enters an anamorphic telescope 22. This produces a beam approximately 20 mm square at its output.

The radiation is then directed by a mirror 23 into a double lens array beam homogeniser 24. A first lens array 25 divides the beam into 36 separate beams which are all individually focused, before intercepting corresponding lenses in a second array 26 to give 36 diverging output beams. An output lens 27 deviates each beam so that they overlap at the plane of a mask 2. The distance between the arrays 25, 26 and the distance to the mask 2 is such that the irradiation at the mask 2 is a superposition of images of each of the lenses in the first array 25. This arrangement produces a uniformly illuminated region about 12 mm square at the mask plane.

Three mirrors 28, 29, 30 are interposed between the homogeniser 24 and the mask 2. These serve to make the apparatus more compact. A field lens 3 placed just before the mask 2 focuses the individual illuminating beams into the entrance pupil of a reducing lens 4.

In the case of Example 2 below, the mask 2 consisted of an optical test pattern, commonly known as the "1951 USAF Test Pattern". The mask 2 was fabricated from chromium deposited on a fused silica substrate. The test pattern allowed the resolution of the system to be measured. For the purpose of producing information marks on diamonds, other masks such as one comprising alpha-numerical characters would be used instead. The mask 2 may be fabricated from a plurality of elementary masks. Components of the mask 2 may be changed so that each diamond 7 receives a partially unique mark. Other parts of the mask 2 may be kept the same so that each diamond 7 receives a partially identical mark.

An ultraviolet reflecting mirror 5 introduces a bend into the optical system before the reducing lens 4 in order to allow a CCD camera system 6, sensitive to visible light, to view the process and act as an alignment aid; a monitor screen 31 is shown. The ultraviolet mirror 5 is essentially transparent to visible light so the diamond 7 may be viewed through the mirror 5.

However a small and constant fraction of the laser radiation (about 1%) does pass through the mirror 5. A second CCD camera 32, sensitive to the ultraviolet radiation and known as a beam profiler, forms an image of the mask 2. The image from the beam profiler 32 is captured and processed by a computer 33. Once calibrated, the beam profiler 32 allows the fluence at the surface of the diamond 7 to be measured during processing. This calibration was achieved by using a Joulemeter (model EM500 with a J50 head manufactured by Molectron Detector, Inc. of Portland, Oreg., USA), to compare the total energy delivered to a sample per pulse with the signal from the profiler 32.

In this embodiment, the reducing lens 4 had a focal length of approximately 68 mm. The system had a demagnification of ×10 and a numerical aperture of 0.15. A relatively large aperture is required in order to accommodate the individual beams generated by the homogeniser 24.

The diamond 7 is mounted on a plinth 8 below the reducing lens 4. The plinth facilitates the coincident positioning of the diamond facet to be marked with a plane defined by a reference surface or surfaces incorporated in the plinth 8, for example by using an essentially cylindrical plinth 8 with a recess in the upper surface so that the diamond 7 is accommodated entirely below the surface with the facet to be marked level with the surface, the upper surface being the primary reference surface.

In order to support the diamond 7, a small quantity of material 34 such as "Plasticine" (trade mark) is placed in the recess. The diamond 7 is then pushed into the plinth 8 using for example a flat glass plate until the plate is in complete contact with the primary reference surface. Additionally, if it is desired to place the facet so that the centre of the facet coincides with the centre of the plinth 8, other means may be used to centralise the diamond 7 before it is pushed finally into place. However, if it is the table facet that is to be located, and the diamond 7 is of a round brilliant shape, the conical indentation in the plinth 8 may adequately centre the diamond 7 without further intervention.

A secondary surface may be incorporated into the plinth 8 a controlled distance from the primary reference surface. This surface may be used to locate the plinth 8 into a suitable holder in a cassette 35 so that, once positioned in the cassette 35, the surface to be marked is at a known position relative to the cassette 35. The cassette 35 is itself mounted on a three axis translation stage 10 so that the desired region of the surface may be placed at the focus of the image of the mask produced by the reducing lens 4.

A cell 9 which encloses the diamond 7 and the plinth 8 is fitted with a window 36 to allow the radiation to enter. The cassette 35 constitutes the base of the cell 9. For the purpose of experimentation, a cell 9 was constructed to be vacuum tight and was connected to a vacuum pump system that allowed gasses of various pressures to be present in the cell 9 during the irradiation. Since it is not usually desirable to work at reduced pressures, the cell 9 need not be so constructed—indeed as the etching proceeds at a satisfactory rate in air, it may be omitted altogether.

A laser rangefinder system (not shown) such as that supplied by Exitech, may be used to help ensure that the plane of the diamond surface coincides with the plane of best focus for the image of the mask. Hence two further windows 37, 38 may be provided in the cell 9. These allow the beam from the rangefinder to enter the cell 9, reflect from the surface of the diamond 7, and leave the cell 9 to enter the detection side of the rangefinder. As the focus adjustment of the stage 10 is adjusted, the point of intersection of the (fixed) rangefinder beam and the diamond facet to be marked moves. The apparent position of this point relative to the (again fixed) detection side of the rangefinder is detected. Once calibrated, this position may be used as a measure of the height of the diamond surface relative to the image of the mask 2.

EXAMPLE 1

Using Apparatus as in FIG. 1

The laser 1 produced pulses of approximately 30 nanoseconds duration at a rate of 20 Hz. It would be preferable to use a laser with a higher repetition rate, eg 200 Hz, to complete the mark more quickly. The fluence at the diamond 7 was set in the range of 0.2–1.2 $J/cm^2$ per pulse, a preferred value being about 0.85 $J/cm^2$ per pulse. Typically, in air (20% oxygen, 80% nitrogen), marks 10–20 nm deep were produced (in 50 seconds) with 1000 pulses. For a given set of process conditions, the depth of the mark is proportional to the number of pulses used in its formation. When the process was carried out in air but with nitrogen purging, ie in an atmosphere of nitrogen with a small percentage of oxygen, etching occurred at a greatly reduced rate; it is believed that no etching would occur in an atmosphere of pure nitrogen. When the process is carried out in a good vacuum ($10^{-6}$ mbar), no observable etching takes place.

The marks produced were a sequence of alpha-characters approximately 50 micron high, and were examined by optical microscopy including the use of an interference microscope to measure the depth profiles. The marks were of a very high quality with no evidence of darkening. Lines as narrow as 1.5 microns have been produced. On larger marks, the bottom of the marks were as smooth as the polished diamond surface. The very fine polishing lines that can typically be observed on polished diamonds tend to be replicated by the process. The depth profile of the lines often showed systematic fluctuations in depth near the edges, called coherence artifacts. This is attributed to the variation in laser fluence caused by the effects of diffraction and of the coherence of the laser source.

Shallow information marks were produced on the tables of good quality gem diamonds. An expert with a ×10 loupe was unable to see the marks, and was satisfied that the mark did not detract from the clarity or value of the stones.

EXAMPLE 2

Using the Apparatus of FIG. 2

Diamond surfaces of various crystallographic orientation were irradiated using the apparatus of the second embodiment. The temperature was room temperature. The mask 2 was the 1951 USAF test target. Each irradiated region of the sample was exposed for 4 minutes at a pulse rate of 50 Hz, to deliver 12000 pulses.

It was first observed that the marks produced were of a very high quality with no evidence of the coherence artifacts present in Example 1. Since the irradiation was more uniform, it was possible to work with higher average fluences than in Example 1 without any risk of blackening or ablation near the edges of the marks. Specifically, when working with a reagent atmosphere of oxygen at atmospheric pressure, the maximum fluence that could be safely used was about 1.8 J/cm$^2$ for <110> orientation surfaces, 2.0 J/cm$^2$ for <111> surfaces and in excess of 2.2 J/cm$^2$ for <100> surfaces.

To determine the importance of a reagent atmosphere, a series of irradiations was undertaken at different pressures of oxygen. The pressures ranged from $10^{-6}$ mbar to 1000 mbar (1000 mbar=$10^5$ Pascals). A Penning gauge was used to measure the pressure between $10^{-6}$ and $10^{-3}$ mbar. A Pirani gauge covered the range $10^{-3}$ to $10^2$ mbar. A mechanical dial gauge covered the range $10^2$ to $10^3$ mbar. Care was taken to ensure the gauges agreed at the cross over points. However, systematic errors in the pressure readings are possible. To control the pressure, oxygen was admitted continuously from a cylinder via a regulator, flow meter and needle valve. For pressures above $10^{-1}$ mbar this was impractical so the apparatus was filled to the desired pressure at the start of run with the pump valved off.

Figure 3:
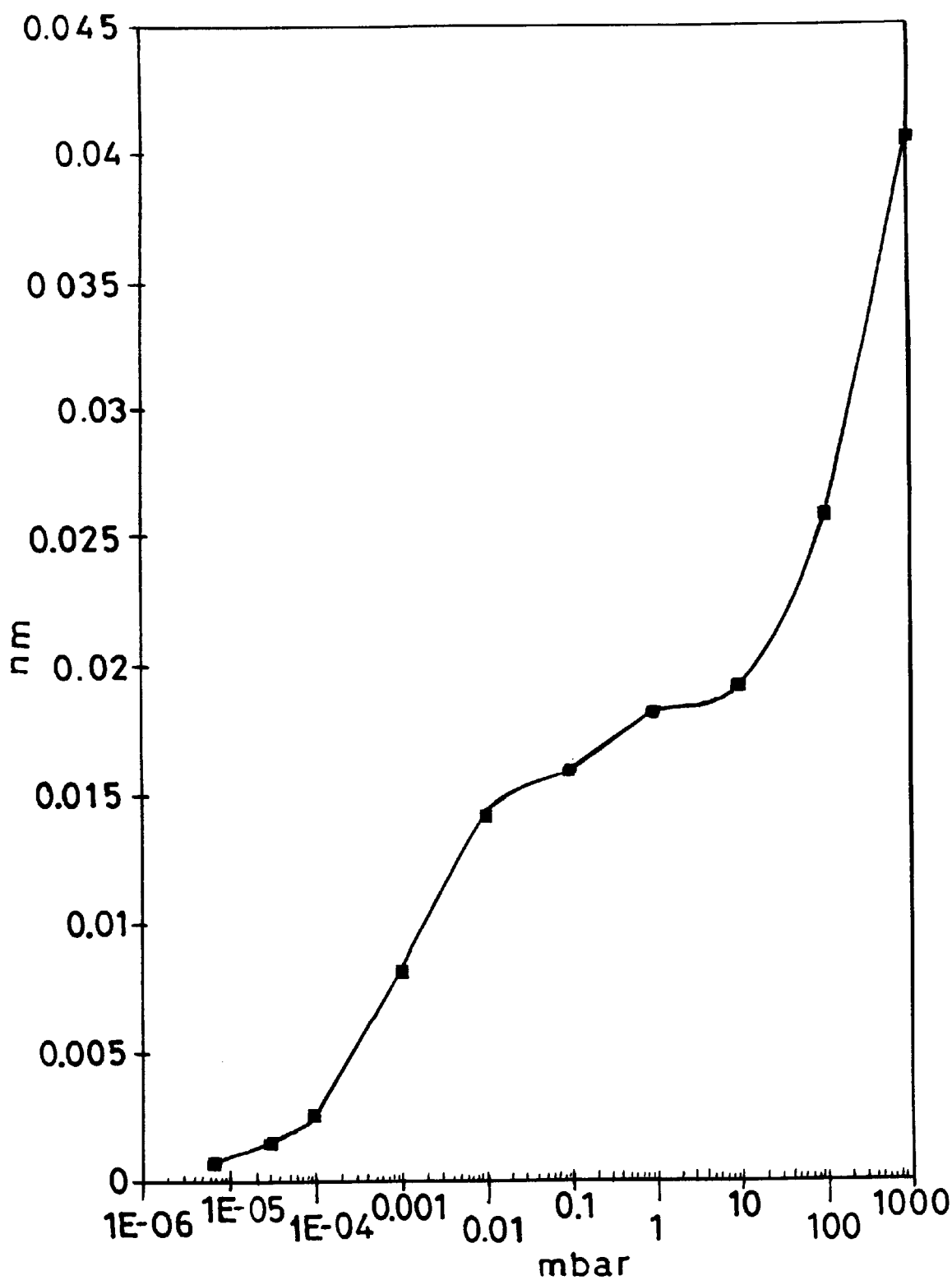
FIG. 3 is a graph of depth etched per pulse, in nm, against presence of oxygen in mbar.

The depths of the marks were measured with the "Micromap" for regions where the test pattern was well resolved. The etch rate (depth per pulse) was calculated. A typical set of results is plotted as a graph in FIG. 3. For that sample, the etch rate at 1000 mbar of oxygen and a fluence of about 1.8 J/cm$^2$ was about 0.042 nm per pulse, equivalent to about 0.23 atomic layers per pulse. The sample surface had <111> orientation. Using these conditions, an information mark of satisfactory depth (eg 10 nm) could be produced in about 5 seconds (about 250 pulses).

At lower pressures, the etch rate reduces until, at the lowest pressure achieved in the apparatus (6.5×$10^{-6}$ mbar), the etch rate was reduced to about 1.7% of the rate at 1000 mbar. Had the sample not been exposed to many more pulses than is desirable for marking (12000 rather than about 250), the mark produced at the lowest pressure would have been too shallow to observe.

At intermediate pressures (eg between $10^{-2}$ and 10 mbar), complicated and often anomalous behaviour was observed. Depending on the sample orientation and the fluence, it was observed that sometimes the etch rate remained constant or even reduced as the oxygen pressure was increased. Careful inspection of the samples using a metallurgical microscope showed that this anomalous behaviour was associated with the existence of partially non-diamond "modified" layers of material at the bottom of the marks. As the layers produced were darker than the surrounding diamond, they rendered the marks more visible than is desirable.

Moreover when a sample was irradiated under conditions known to cause the formation of the undesirable layers (eg 1 mbar oxygen pressure and 1.7 J/cm$^2$ for a <110> sample) to produce an observable layer and then subsequently irradiated at a higher pressure (eg 100 mbar), the modified layer was quickly removed. Hence one may conclude that the formation of the modified layers is associated with attempting to etch with an inadequate supply of oxygen. Provided enough oxygen is present, the modified layers are removed as fast as they form.

The present invention has been described above purely by way of example, and modifications can be made within the spirit of the invention.

What is claimed is:

1. A method of producing on a polished facet of a diamond gemstone an information mark which is invisible to the naked eye, comprising irradiating the respective portion of the facet surface with radiation having a wavelength shorter than about 400 nm, in the presence of a reagent which reacts with the irradiated portion of the facet surface and causes a mark to be formed, there being no substantial darkening in the formed mark.

2. A method of producing on a polished facet of a diamond gemstone an information mark which is invisible to the naked eye, comprising irradiating the respective portion of the facet surface with radiation having a wavelength shorter than about 400 nm, in the presence of a reagent which reacts with the irradiated portion of the facet surface and causes a mark to be formed, the fluence of the irradiation being below the level at which substantial darkening is caused to be present in the formed mark.

3. A method of producing on a polished facet of a diamond gemstone an information mark which is invisible to the naked eye, comprising irradiating the respective portion of the facet surface with radiation having a wavelength shorter than about 400 nm, in the presence of a reagent which reacts with the irradiated portion of the facet surface and causes a mark to be formed, the formed mark being such that is does not detract from the clarity grade of the diamond.

4. A method of producing on a polished facet of a diamond gemstone an information mark which is invisible to the naked eye, comprising irradiating the respective portion of the facet surface with radiation having a wavelength shorter than about 400 nm, in the presence of a reagent which reacts with the irradiated portion of the facet surface and causes a mark to be formed, the fluence of the irradiation being below the level at which the formed mark detracts from the clarity grade of the diamond.

5. A method of producing on a polished facet of a diamond gemstone an information mark which is invisible to the naked eye, comprising irradiating the respective portion of the facet surface with radiation having a wavelength shorter than about 400 nm, in the presence of a reagent which reacts with the irradiated portion of the face surface and causes a mark to be formed, the fluence being below the ablation threshold of the diamond and being below the level at which substantial darkening is caused to be present in the formed mark.

6. The method of claim 1, wherein the radiation is pulsed and the respective portion is irradiated with not fewer than about 100 pulses per location irradiated.

7. The method of claim 1 wherein the radiation is pulsed and the fluence at the location irradiated is not more than about 3 J/cm$^2$ per pulse.

8. The method of claim 1 wherein the radiation is pulsed and the fluence at the location irradiated is not more than about 2 J/cm$^2$ per pulse.

9. A method of producing an information mark on a polished facet of a diamond gemstone, comprising irradiating the respective portion of the facet surface with radiation having a wavelength shorter than about 400 nm, the fluence at the location irradiated not being more than about 3 $J/cm^2$ per pulse and not fewer than about 100 pulses being used per location irradiated, in the presence of a reagent which reacts with the irradiated portion of the facet surface and causes a mark to be formed.

10. The method of claim 9 wherein the fluence at the location irradiated is not more than about 2 $J/cm^2$ per pulse.

11. The method of claim 9 wherein no substantial darkening occurs in the mark during the formation of the mark.

12. The method of claim 9 wherein the formed mark is invisible to the naked eye aided with a ×10 loupe.

13. The method of claim 9 wherein no visually detectable non-diamond carbon is present in the formed mark.

14. The method of claim 9 wherein the respective portion is irradiated with radiation having a wavelength of less than 225 nm.

15. The method of claim 9 wherein the radiation is pulsed and the depth of said mark is monitored during the process and controlled by the number of pulses applied.

16. The method of claim 9 wherein the information mark is produced on the table of the diamond gemstone.

17. The method of claim 9 wherein said reagent is a gas.

18. The method of claim 17 wherein said reagent is an oxidising gas.

19. The method of claim 18, wherein said reagent is air.

20. The method of claim 9 wherein the information mark has a depth of not more than about 100 nm.

21. The method of claim 9 wherein the information mark has a depth of not less than about 1 nm.

* * * * *